United States Patent
Cardelius et al.

(10) Patent No.: US 9,333,312 B2
(45) Date of Patent: May 10, 2016

(54) PEEP REGULATION FOR A BREATHING APPARATUS

(75) Inventors: Erik Cardelius, Djursholm (SE); Mathias Eklund, Stockholm (SE)

(73) Assignee: Maquet Critical Care AB, Solna (SE)

(*) Notice: Subject to any disclaimer, the term of this patent is extended or adjusted under 35 U.S.C. 154(b) by 1060 days.

(21) Appl. No.: 13/260,588

(22) PCT Filed: Mar. 27, 2009

(86) PCT No.: PCT/EP2009/053699
§ 371 (c)(1),
(2), (4) Date: Mar. 9, 2012

(87) PCT Pub. No.: WO2010/108552
PCT Pub. Date: Sep. 30, 2010

(65) Prior Publication Data
US 2012/0167884 A1     Jul. 5, 2012

(51) Int. Cl.
*A61M 16/00* (2006.01)
*A61M 16/10* (2006.01)
*A61B 5/091* (2006.01)
*A61M 16/20* (2006.01)

(52) U.S. Cl.
CPC ............. *A61M 16/0051* (2013.01); *A61B 5/091* (2013.01); *A61M 16/20* (2013.01); *A61M 16/202* (2014.02); *A61M 16/205* (2014.02); *A61M 2016/0027* (2013.01); *A61M 2016/0039* (2013.01); *A61M 2016/0042* (2013.01)

(58) Field of Classification Search
CPC ............. A62B 7/14; B64D 2013/0677; B64D 2013/0681; B64D 2231/00; B64D 2231/02
USPC .............. 128/204.18, 204.21, 204.23, 204.26
See application file for complete search history.

(56) References Cited

U.S. PATENT DOCUMENTS

| | | | | |
|---|---|---|---|---|
| 5,931,162 | A * | 8/1999 | Christian ................ | 128/204.23 |
| 5,975,748 | A * | 11/1999 | East et al. ................. | 703/6 |
| 6,564,798 | B1* | 5/2003 | Jalde ........................ | 128/205.24 |
| 7,011,091 | B2* | 3/2006 | Hill et al. ................. | 128/204.18 |
| 8,474,455 | B2* | 7/2013 | Soliman et al. .......... | 128/204.21 |
| 2003/0168066 | A1 | 9/2003 | Sallvin | |
| 2007/0062533 | A1 | 3/2007 | Choncholas et al. | |
| 2007/0151563 | A1* | 7/2007 | Ozaki et al. ............. | 128/204.23 |
| 2008/0163872 | A1* | 7/2008 | Negele et al. ............ | 128/204.21 |
| 2009/0301492 | A1 | 12/2009 | Wysocki et al. | |

* cited by examiner

*Primary Examiner* — Valerie L Skorupa
*Assistant Examiner* — Douglas Sul
(74) *Attorney, Agent, or Firm* — Schiff Hardin LLP

(57) ABSTRACT

A breathing apparatus has an expiratory flow sensor unit, an expiratory pressure sensor unit, an expiratory pressure regulator, and an expiratory control unit operatively connected to the expiratory pressure sensor unit for a feedback control of an expiratory pressure during an expiratory phase of a breathing cycle. The expiratory control unit is adapted to provide a real time target pressure value during the expiratory phase to the expiratory pressure regulator for adjusting a desired positive end expiratory pressure (PEEP) level ($PEEP_{set}$) based on an inspiratory tidal volume of an inspiratory phase of the same breathing cycle and a currently accumulated expiratory tidal volume measured by the expiratory flow sensor unit. In this manner advantageous regulation of PEEP with minimized work of breathing is obtained.

19 Claims, 5 Drawing Sheets

PEEP REGULATION FOR A BREATHING APPARATUS

BACKGROUND OF THE INVENTION

1. Field of the Invention

This invention pertains in general to the field of breathing apparatuses and expiratory regulation thereof. More particularly the invention relates to regulation of expiratory pressure by means of an expiratory pressure regulator in such a breathing apparatus, and methods therefor. Even more particularly, the invention relates to regulation of expiratory pressure during an expiratory phase of a breathing cycle to obtain a desired positive end expiratory pressure (PEEP).

2. Description of the Prior Art

Various breathing apparatuses are arranged to provide a user-selectable desired positive end expiratory pressure (PEEP). Such apparatuses include intensive care ventilators, anesthesia machines, etc. However, the actual PEEP obtained may deviate from the user-selected desired PEEP for a variety of reasons. Such deviations may for instance occur due to changes in the patient situation or system during ventilation, e.g. a breathing cycle, such as patient changes, e.g. changes of patient position in a bed; system changes, like changes of tubing, filter changes, humidity moisture exchanger (HME) insertion, accumulation of humidity; etc.

In U.S. Pat. No. 6,564,798 of the same proprietor as the present application, a method for controlling an expiratory valve in a ventilator during expiration is disclosed. During expiration, the method comprises a first interval in which the expiratory valve is opened completely. During this first interval no active control of expiratory pressure is carried. A determination is made when the flow or pressure in the expiratory phase meets a predefined condition. A second interval is started when the flow in the expiratory part meets the condition. The expiratory valve is regulated during the second interval in order to attain a pre-set positive end expiratory pressure (PEEP) pressure in the patient. However, no details are given in U.S. Pat. No. 6,564,798 how this regulation is carried out. Furthermore, in breathing apparatus working on a bias flow, a new inspiratory cycle may be triggered when no gas flow is available for adjusting the expiratory pressure during regulation.

In US 2003/168066 A1 of the same applicant as the present application, an expiratory valve for regulating gas pressure within an expiration gas flow is disclosed. The regulation is carried out dependent on an input regulatory signal and an expiratory pressure sensor. A control unit is coupled to the expiratory valve and to the expiratory pressure sensor for calculating a target pressure as a function of time. The target pressure is dependent on a value of compliance calculated from measurements of pressure and inspired volume of provided breathing gas made during an inspiration phase. Compliance is calculated from $\Delta V$, the change in volume, divided by $\Delta P$, the change in pressure of the system comprising inspiratory tubing and the patient lung. Expiratory pressure is controlled based on the regulatory signal dependent on a magnitude of the difference between the target pressure and the actual pressure. However, reliability of the method disclosed in US 2003/168066 A1 may be improved, as compliance is a non-constant parameter and may even change during a single breathing cycle, i.e. the compliance calculated during inspiration may change during a single expiration. Compliance may e.g. change due to the patient moving, etc. In more detail, a major drawback with the method disclosed in US 2003/168066 A1 is that the pressure curve is defined during inspiration by means of a calculated time constant based on the calculated inspiratory compliance. However, the actual time constant in a real breathing circuit differs from this calculated time constant. The actual time constant is in fact dependent on the product of compliance AND the flow resistance. It is not possible to make any conclusion of the flow resistance and hence the time constant based solely on the value of the compliance. The flow resistance depends on the properties of the patient lung and the endotracheal tube, etc, and these factors are independent of the compliance. In addition, the actual time constant may change during the course of exhalation of a single breathing cycle, and thus the estimate disclosed in US 2003/168066 A1 is not suitable for a number of clinical situations.

Furthermore, it is desired that expiratory work of breathing of patients ventilated with breathing apparatuses is minimized.

Thus, there is a need for an improved method of regulating expiratory pressure and reliably achieving a desired PEEP.

Hence, an improved breathing apparatus and method of regulating expiratory pressure would be advantageous, and in particular allowing for increased flexibility, reliability, and patient safety would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a breathing apparatus, a method, and a computer program product, according to the appended patent claims.

This object is obtained by providing an expiratory target pressure reference curve in a breathing apparatus that depends on how much of an inspired tidal volume of a breath cycle has been currently expired during an expiratory phase of the same breathing cycle.

The present method and apparatus are not based on parameters or measurements between different breathing cycles. The regulation is not iterative, but based on a breath by breath basis. Iterative solutions have the drawback that iterative methods do not take changes of e.g. the patient lung compliance between different breathing cycles. In contrast, the present method is based on a correct measured inspiratory tidal volume of the same breathing cycle.

According to a first aspect of the invention, a breathing apparatus is provided according to claim 1. In an embodiment the breathing apparatus comprises an expiratory flow sensor unit, an expiratory pressure sensor unit, an expiratory pressure regulator, and an expiratory control unit operatively connected to the expiratory pressure sensor unit for a feedback control of an expiratory pressure during an expiratory phase of a breathing cycle. The expiratory control unit is adapted to provide a real time variable target pressure ($P_{target}$) during the expiratory phase to the expiratory pressure regulator for regulating a desired positive end expiratory pressure (PEEP) level ($PEEP_{set}$). The target pressure ($P_{target}$) is provided based on an inspiratory tidal volume ($VT_i$) provided by the breathing apparatus of an inspiratory phase of the same breathing cycle and a currently accumulated expiratory tidal volume ($VT_e$) measured by the expiratory flow sensor unit.

According to another aspect of the invention, a method is provided according to the appended independent method claim. In an embodiment the method is a method of internally controlling an expiratory pressure regulator of a breathing apparatus during an expiratory phase of a breathing cycle. The breathing apparatus may be provided according to the first aspect. The method comprises measuring an inspired tidal volume (VTi) delivered from the breathing apparatus during an inspiratory phase of the breathing cycle; and subsequently, during the expiratory phase, measuring a flow of expiratory gas by an expiratory flow sensor unit, calculating an accumulated expiratory tidal volume (VTe) of the expiratory phase, and providing a real time target pressure to the expiratory pressure regulator for regulating towards a desired positive end expiratory pressure (PEEP) level (PEEPset) based on the inspiratory tidal volume (VTi) of the inspiratory phase of the same breathing cycle, and a currently accumulated expiratory tidal volume (VTe).

In an embodiment the method is performed in-vitro, without a patient being connected to the breathing apparatus.

According to a further aspect of the invention, a computer program product, storable on a computer readable medium, is provided for processing by a computer. The computer program product comprises code segments for internally controlling an expiratory pressure regulator of a breathing apparatus during an expiratory phase of a breathing cycle. The code segments comprise a first code segment for measuring an inspired tidal volume ($VT_i$) delivered from the breathing apparatus during an inspiratory phase of the breathing cycle; and a second code segment for subsequently, during the expiratory phase, measuring a flow of expiratory gas by an expiratory flow sensor unit, a third code segment for calculating an accumulated expiratory tidal volume ($VT_e$) of the expiratory phase, and a fourth code segment for providing a real time target pressure to the expiratory pressure regulator (59) for regulating towards a desired positive end expiratory pressure (PEEP) level ($PEEP_{set}$) based on the inspiratory tidal volume ($VT_i$) of the inspiratory phase of the same breathing cycle, and a currently accumulated expiratory tidal volume ($VT_e$).

Further embodiments of the invention are defined in the dependent claims, wherein features for the second and subsequent aspects of the invention are as for the first aspect mutatis mutandis.

Some embodiments of the invention provide for quick expiratory release of gas from the patient and then maintaining a desired PEEP in the patient lungs.

Some embodiments of the invention also provide for minimized work of breathing, i.e. the patient is provided for ease of exhalation.

Some embodiments of the invention provide for a reliable consideration of changes in lung mechanics during a single breathing cycle.

Some embodiments of the invention provide for reliable prevention of triggering a new inspiration before the end of expiration, as a value of a bias flow is observed and not under passed.

Some embodiments of the invention provide for reliable minimization of work of breathing for various types of lungs.

Some embodiments of the invention provide for a reliable pressure regulation without instabilities.

Embodiments of the invention provide for automatically minimizing the expiratory resistance for various types of lungs.

It should be emphasized that the term "comprises/comprising" when used in this specification is taken to specify the presence of stated features, integers, steps or components but does not preclude the presence or addition of one or more other features, integers, steps, components or groups thereof.

DESCRIPTION OF THE PREFERRED EMBODIMENTS

Figure 1:
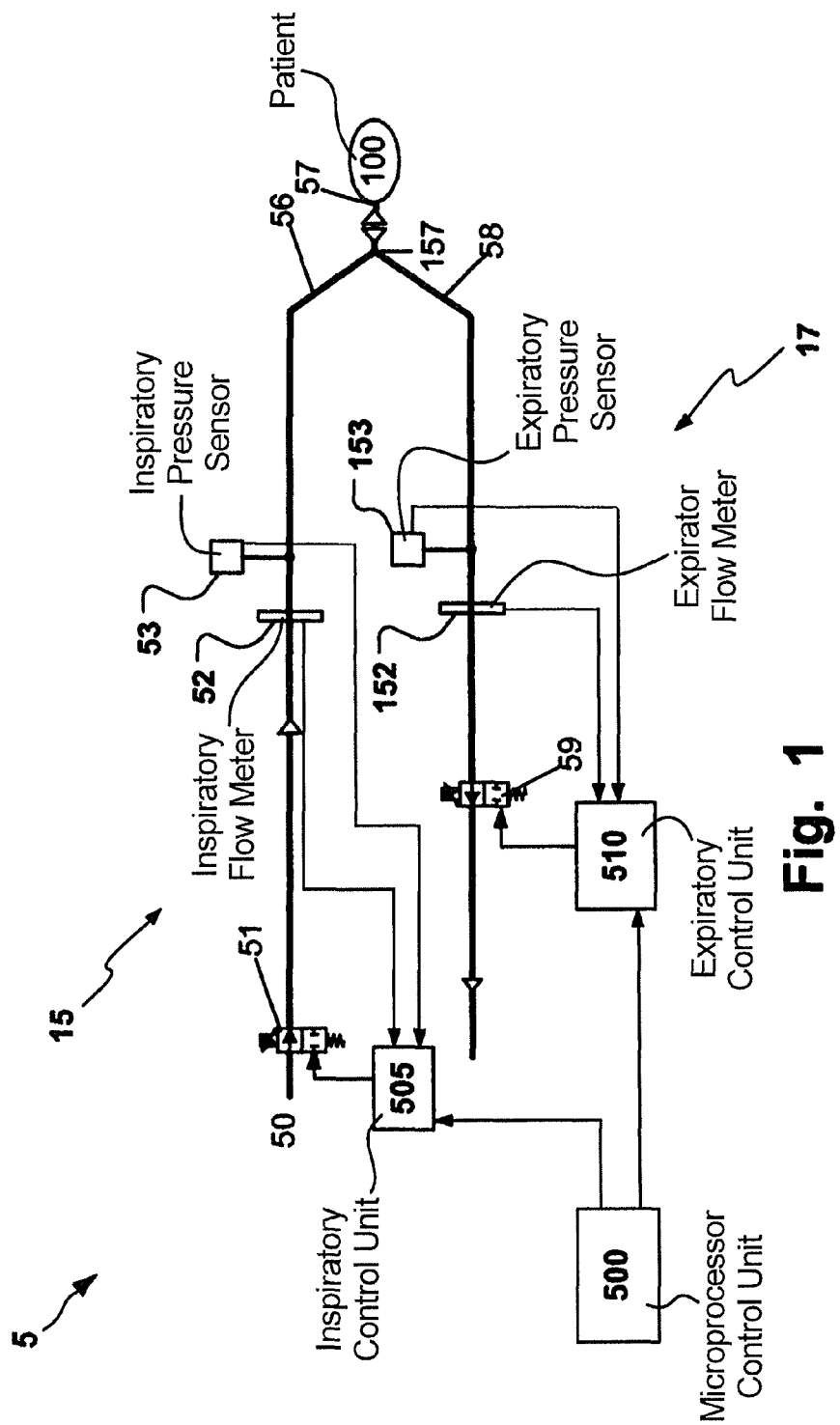
FIG. 1 is a schematic illustration of a breathing apparatus comprising a control unit for expiratory pressure regulation to a desired level of PEEP.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a breathing device having an inspiratory and an expiratory branch. However, it will be appreciated that the invention is not limited to the illustrated embodiment of a medical ventilator, but may be applied to many other breathing apparatuses, including for example anesthesia machines having breathing circles, CO2 absorbers, volume reflectors, etc. All applications have in common that a PEEP is advantageously regulateable by embodiments of the invention.

In FIG. 1, the direction of gas flow is illustrated by triangular arrows. In the embodiment, a breathing apparatus, here represented by a medical ventilator 5, is shown as having an inspiratory gas flow section 15 and an expiratory gas flow section 17. In other embodiments, the breathing apparatus may be an anesthetic breathing apparatus. The anesthetic breathing apparatus may comprise a circle system. All embodiments of breathing apparatuses have in common that they comprise an expiratory gas flow section that handles gas expired from a patient during an expiratory phase of a breathing cycle.

The inspiratory gas flow section 15 of the illustrated embodiment is adapted for connection to one or more sources of gas 50, for instance oxygen and air, as well as to an inspiration line 56. The inspiratory gas flow section 15 includes a regulatory arrangement 51 to regulate gas flow from the one or more gas sources 50 and provides a breathing gas into the inspiration line 56 during an inspiration phase of a patient breathing cycle. An inspiratory flow meter 52 and an inspiratory pressure sensor 53 are provided in the inspiratory section 15 to measure, respectively, the flow and pressure of breathing gas passing into the inspiration line 56. Other embodiments may comprise suitably arranged vaporizers for administration of an anesthetic agent with the inspiratory gas flow to the patient. In addition, a circle system may in another embodiment provide a degree of re-breathing of earlier expired patient gas, including units for conditioning the circulated gas, such as $CO_2$ absorbers. In the latter case, a fresh gas flow is controlled by regulatory arrangement 51 to suitably replenish gas contents in the breathing circle.

The expiratory gas flow section 17 is adapted to connect to an expiration line 58 and includes an expiratory pressure regulator 59, such as a solenoid valve. The expiratory pressure regulator 59 is adapted to control the pressure, and thus indirectly the flow of expiration gas from the airways of a patient 100. An expiratory flow meter 152 is also arranged in the expiratory gas flow section 17. The expiratory pressure regulator 59 is adapted to regulate the gas pressure within the expiratory gas flow section 17 and airways of the patient 100 during an expiration phase of a patient breathing cycle. An expiratory pressure sensor 153 is provided to measure expiration gas pressure and is, in this embodiment, located within the expiratory gas flow section 17 of the ventilator 5, proximal the expiratory pressure regulator 59.

A conduit 57, such as an endotracheal tube, is arranged to provide a common gas flow path for breathing gas passing from the inspiration line 56 to the airways of patient 100 and expiration gas passing into the expiration line 17 from the airways of patient 100.

In embodiments comprising a circle system (not illustrated), check valves may be arranged suitably to support the correct direction of gas flow.

A microprocessor control unit 500 is also included within the ventilator 5 and is here operatively connected to both as an inspiratory control unit 505 and an expiratory control unit 510.

The inspiratory control unit 505 generates and transmits control signals to the inspiratory regulatory arrangement 51. The control signals are typically generated dependent on gas parameters measured by one or both of the inspiratory flow meter 52 and the inspiratory pressure sensor 53 and on a desired mode of delivery. The choice of delivery mode and the parameters of which will be measured are typically selected by an operator of the ventilator 5 but which may be selected automatically, for example based on a monitored respiratory action of the patient 100. This regulatory arrangement 505 then operates in response to these control signals to regulate the supply of the breathing gas into the inspiration line 56.

Figure 2:
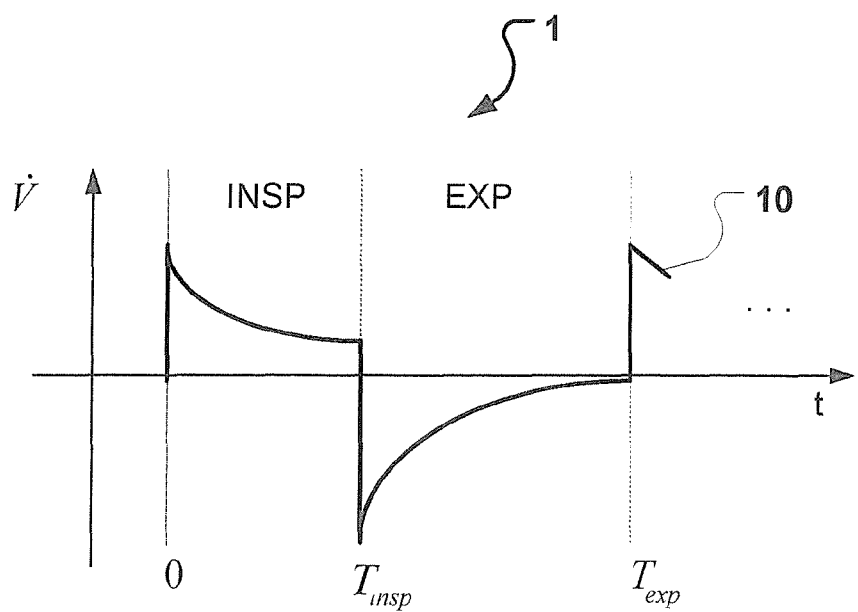
FIG. 2 is a graph illustrating a typical flow profile during a pressure controlled breathing cycle, wherein $\dot{V}$ is the flow of volume from the breathing apparatus in accordance with a reference condition i.e. compensated for a given pressure and temperature.

In FIG. 2 a typical flow profile 10 during a pressure controlled breathing cycle is shown in a graph 1. $\dot{V}$ is the flow of volume from the breathing apparatus in accordance with a reference condition i.e. compensated for a given pressure and temperature. $\dot{V}$ has a positive value during the inspiratory phase INSP, as a positive gas flow is provided into the patient via inspiratory gas flow section 15 to the patient 100 between the start of inspiration at time 0 and the end of inspiration at time $T_{insp}$. $\dot{V}$ has negative values during the expiratory phase EXP, as a gas flow is provided out of the patient into the breathing apparatus via the expiratory gas flow section 17 between the end of inspiration (=start of expiration) at time $T_{insp}$ and the end of expiration at time $T_{exp}$. Thereafter, a new breathing cycle is started with a subsequent inspiratory phase.

Based on measurements from the inspiratory gas flow meter 52, an inspiratory tidal volume $VT_i$ is determined as the volume of gas inspired by the patient 100 during an inspiratory phase of a breathing cycle. The inspiratory tidal volume $VT_i$ may be readily calculated by integrating, in a known manner, the output from the flow meter 52 throughout the inspiration phase. $VT_i$ may also be determined by other means, e.g. by metering gas supplied by gas sources 50.

The expiratory control unit 510 generates and transmits control signals to the expiratory pressure regulator 59. These control signals are, during an expiration phase, generated in response to pressure signals from the expiratory pressure sensor 153 and the expiratory flow meter 152 to achieve a desired PEEP pressure.

The manner in which the expiratory control means 510 operates to generate the control signals will be described in more detail hereinafter.

The expiratory control unit 510 is programmed to operate as a feedback type controller in that the control signals are generated from a comparison between an actual pressure, as measured by the pressure sensor 153, and a target pressure, generated by the control means 510 according to a control algorithm.

By means of the control algorithm, the expiratory pressure regulator 59 is operated to permit a flow of expiration gas, taking into account the requirement to achieve a desired PEEP level, $PEEP_{set}$. In order to regulate the lung pressure, as indicated from measurements by the expiratory pressure sensor 152 in the ventilator 5, to $PEEP_{set}$ as quickly as possible it is preferable that the control algorithm is designed to permit the measured pressure to fall below $PEEP_{set}$ before $PEEP_{set}$ is reached.

It should be noted that the pressure measured by the expiratory pressure sensor 153, as in the illustrated embodiment located in the expiratory gas flow section 17, will be less than that within the lungs of patient 100 while there exists an expiration gas flow. This deviation is due to a pressure drop along the expiratory gas flow section 17, and in the endotracheal tubes and the lungs, as long as a gas flow is present therein.

Alternatively, the expiratory pressure may be measured from a pressure sensor located at the Y-piece 157, eliminating the pressure difference due to the pressure drop along the expiratory gas flow section 17, except the endotracheal tubes and the lungs.

Figure 3:
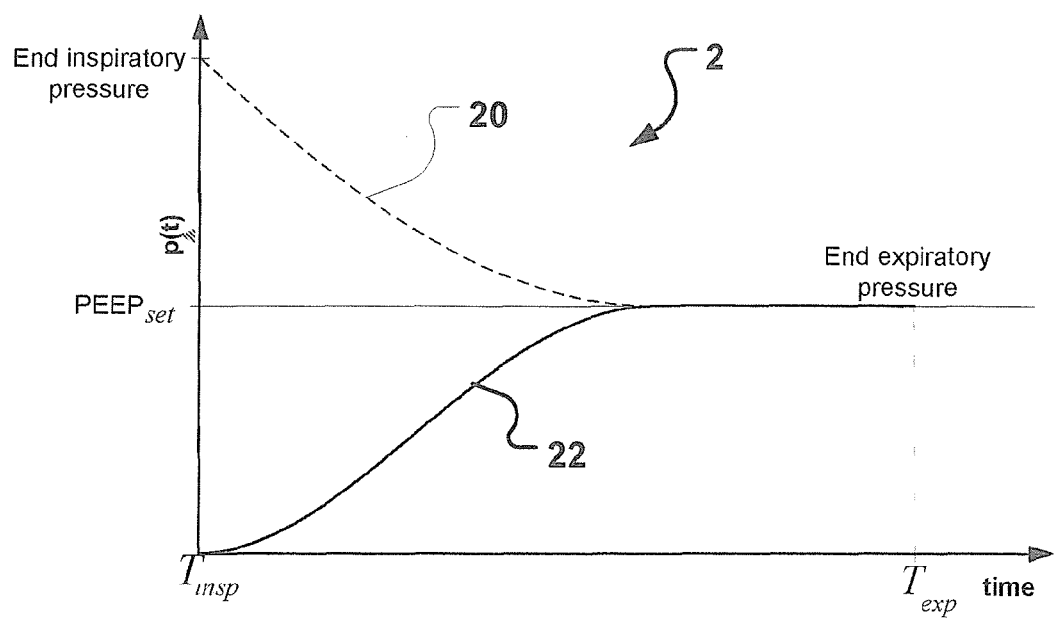
FIG. 3 is a graph illustrating patient lung pressure and a target pressure for a desired PEEP level during an expiratory phase of a breathing cycle.

Thus, even though the measured expiratory pressure may be allowed to fall below $PEEP_{set}$ it is chosen to not be allowed to fall so much that pressure within the lungs falls to a level below $PEEP_{set}$ during regulation. FIG. 3 is a graph 2 illustrating such a relation of a patient lung pressure 20 (dashed line) and a target expiratory pressure 22 (continuous line) for a desired $PEEP_{set}$ level during an expiratory phase of a breathing cycle.

Figure 4:
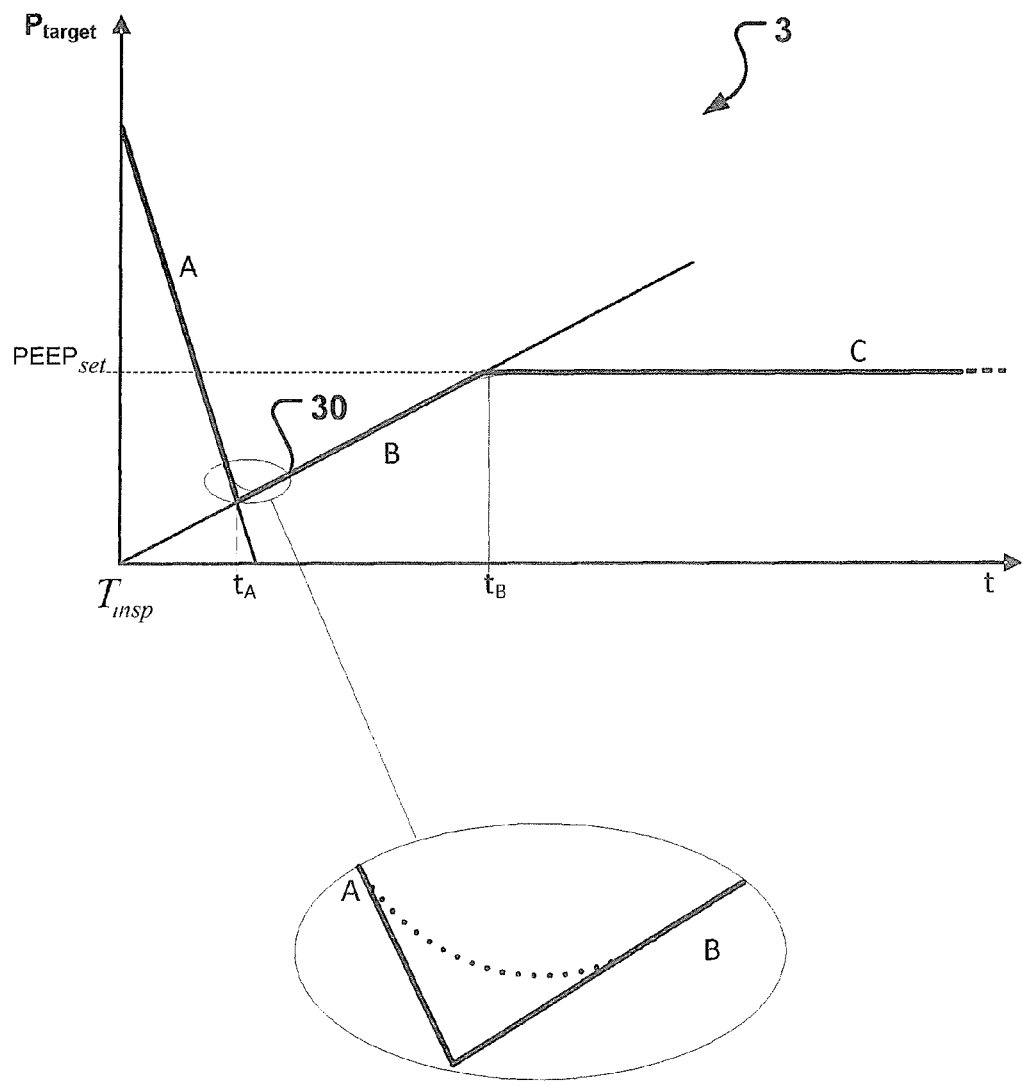
FIG. 4 is a graph illustrating different phases of expiratory pressure regulation in a method.

Regardless of whether the initial pressure is permitted to fall below $PEEP_{set}$, the control algorithm is adapted to generate the target pressure, $P_{target}$ target 30, as a function of time, t, and dependent on a value of expired gas volume, as illustrated in FIG. 4. The expired gas volume is for instance measured by expiratory gas flow meter 152, or provided by other units.

The expiratory tidal volume $VT_e$ may be identical, or vary from the inspired tidal volume $VT_i$ of one and the same breathing cycle.

The control algorithm of expiratory control unit 510 is based on a tidal volume control parameter. The control algorithm is adaptive to various conditions of this tidal volume control parameter, as will be elucidated further below. The control algorithm is provided to adapt to a particular patient and to changes in control conditions, such as changes of lung compliance or resistance during or within a single breathing cycle in progressing mechanical ventilatory assistance.

This advantageous control algorithm will be elucidated in more detail below.

The primary task of a PEEP feedback control is to release gas out of the patient's lungs as quickly as possible and with as low work of breathing as possible for the patient. During, or at the end of the expiratory phase, expiratory gas release is stopped, and a desired PEEP is obtained and kept in the lungs of the patient 100.

Furthermore, the expiratory pressure target curve $P_{target}$ 30 to the PEEP regulator 59 works according to the following requirements, amongst others:

The PEEP regulator 59 shall not be opened fully at the beginning of the expiratory phase, e.g. with a current step, as this may potentially excites oscillations in the system, which are difficult to control. A current to the PEEP regulator 59 is chosen to not be changed quicker than the system can physically react, i.e. release gas from the expiratory branch 17 (with or without patient 100 connected).

The expiratory breathing resistance is minimized in a way that considers an up-to date condition of the lung and its mechanics in real time, including all changes during a single breathing cycle.

The same expiratory pressure control algorithm is valid for all types of lungs, independent of compliance, resistance, tidal volume, etc.

The expiratory work of breathing may be minimized by adjusting the expiratory pressure in the ventilator to a pressure that is lower than the desired PEEP, at least during the beginning of the expiratory phase. In this manner the patient may exhale easier. Due to the resistance in the aggregated gas flow path of the breathing apparatus and connected patient tubing as well the anatomical respiratory path of the patient 100, the pressure in the lungs will be higher than the pressure measured by the expiratory pressure sensor, as long as there is an expiratory flow.

Hence, the requirement is that the PEEP level is established when or before the expiratory flow reaches zero, or a bias flow is established, if existent. Otherwise the pressure in the lungs will drop below PEEP and the lungs have to be re-filled with a volume of gas in order to raise the pressure back to PEEP. However, such a re-fill volume requires a flow that either takes a time to produce, or is taken from the bias flow. In case the re-fill volume is taken from the bias flow, this will cause a flow triggering of the subsequent inspiratory phase in case the volume is over a defined trigger volume. However, triggering a new inspiratory phase before the previous expiratory phase is concluded, is both inconvenient and potentially harmful for the patient. The present method avoids such issues.

In order to simplify the description of the target pressure curve $P_{target}$ 30 to the PEEP regulator 59, the curve is schematically subdivided into three sections A, B and C, as illustrated in FIG. 4. Section A covers a phase of quick release of gas. Section B covers a regulation of the patient lung pressure to $PEEP_{set}$. Section C is a phase of constant PEEP wherein $PEEP_{set}$ is maintained until the beginning of a new breathing cycle.

In a practical embodiment, the target pressure provided for regulating the expiratory valve is created according to MAX (A, MIN(B,C)). In order to render the transition from portion A to portion B less abrupt, the slope of curve portion A is reduced when approaching curve portion B, as illustrated in FIG. 4 by the dotted line, which transition is shown enlarged in the encircled portion of FIG. 4.

The following description puts particular emphasis on obtaining the target pressure curve during section B.

Figure 5:
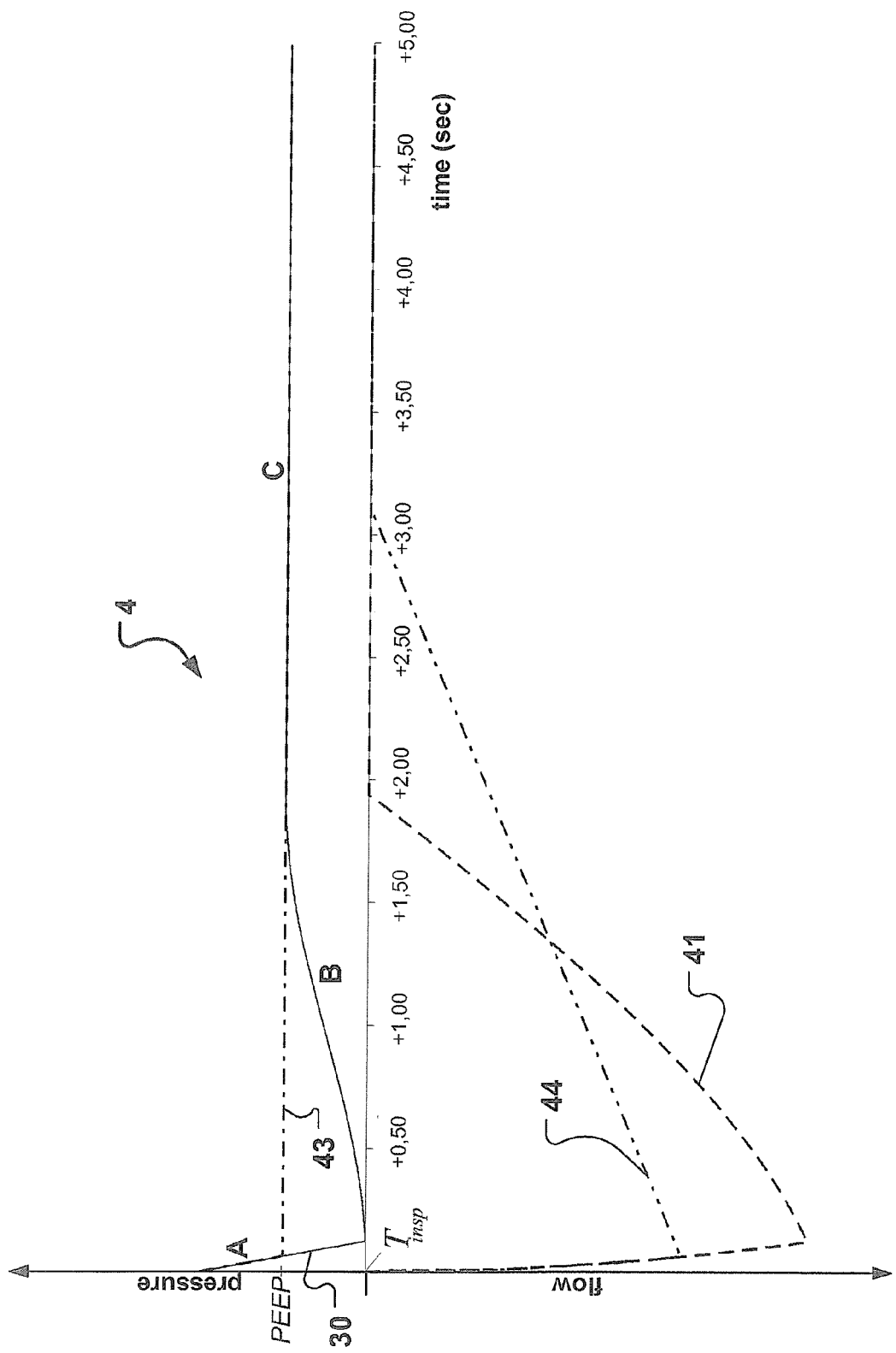
FIG. 5 is a graph illustrating expiratory flow and target pressure for two different methods of regulating a desired PEEP.

Expiratory flow and target pressure for two different methods of regulating patient lung pressure to $PEEP_{set}$ are illustrated in FIG. 5 in an example for a lung of high compliance and low resistance. In FIG. 5, the following curves are shown: 30 volume dependent expiratory regulator target pressure (having sections A, B, C); 41 expiratory flow with volume dependent pressure regulation; 43 constant expiratory regulator target pressure; 44 expiratory flow using constant pressure.

Section A of Target Pressure Curve

The expiratory target pressure curve 30 starts at the end inspiratory pressure level at time Tinsp.

In section A of the curve representing the target pressure, extending until a time $t_A$, a quick release of gas from the patient lungs is provided. The gradient of the curve is chosen to be proportional to a release of expiratory gas based on a calculated compliance of the present patient 100 lung. Pressure regulation in section A, based on the expiratory target pressure curve 30, is performed between a maximum gradient and a minimum gradient. The maximum pressure gradient is present when emptying the lungs the theoretically quickest way. The minimal pressure gradient is present at a pre-determined slower emptying of the lungs, e.g. based on a state of illness or physiology of the patient; see also below.

For stiff lungs (low compliance), the gradient is less than for a flexible lung, i.e. the intersectional point at the x-axis of the imaginary extension of the curve is towards higher values for stiffer lungs.

For small lung volumes a small regulation volume buffer is available. In this case, the pressure is lowered more cautiously. For larger lung volumes, often equivalent to larger compliance values, the curve is steeper in section A.

The maximum gradient of the curve is determined how quickly the systemic volume can be released through the expiratory exhaust of the breathing apparatus. This is the physical limit of the system. This maximum gradient of the curve is for instance determined by measuring how quickly an expiratory pressure falls at the beginning of the expiratory phase, with a plug blocking the Y-piece and opening the expiratory valve completely with a step function. It is physically not possible to release a gas volume from any type of patient lungs quicker than with this determined maximum gradient of the curve. If a target value curve for expiratory pressure is applied that is steeper than this maximum gradient of the curve, merely a deviating error is created in the pressure regulator, which error is not possible to be compensated for. Regulation of the expiratory pressure may become unstable, which is undesired. Therefore, as applicants have realized, the expiratory pressure regulator needs not to open quicker than with this maximum gradient of the curve.

Optimally, it might appear that a target pressure reference should look like a step, i.e. the reference pressure is zero, corresponding to a completely open expiratory valve up to a suitable point in time where the valve closes completely. However, as mentioned above, this would make the regulation instable. Further, this may also be practically impossible to achieve due to the transient time of the system. Therefore, the target pressure curve 30 is kept substantially close to the determined maximum gradient of the curve during section A of the expiratory regulation.

The minimum gradient of the curve is determined by the curve needed to control PEEP with a plug in the Y-piece (compliance/resistance only determined by systemic tubing and patient tubing).

These measures are taken in order to release a maximum volume from the lungs as quickly as possible.

However, the expiratory valve is not opened completely, not even substantially completely, due to the instability reasons given above.

Section B of Target Pressure Curve

Section B extends from time $t_A$ to time $t_B$

The target is to release the patient gas as quickly as possible out of the lungs during the expiratory phase, but still to have sufficient gas volume left to regulate the pressure to the PEEP$_{set}$ level before the expiration flow ends. A bias flow may circulate constantly from the inspiratory gas flow section 15 to the expiratory gas flow section 17, passing the Y-piece 157. When a bias flow is present, the flow in the expiratory gas flow section 17 shall be equal to (only bias flow), or larger (bias flow plus expiratory gas flow from the patient) than the flow in the inspiratory gas flow section 15 (only bias flow) in order to avoid a self trigger of a new breathing cycle. This may be monitored by control unit 500 receiving signals from the inspiratory flow meter 52 and the expiratory flow meter 152.

The expiratory flow curve provides information about the resistance in the lungs, i.e. how quick the gas is released from the lungs. The difference in time between the point in time when the expiratory flow is zero (or equal to the bias flow) and the point in time when a stable PEEP is attained, see FIG. 5, is a measure for the inefficiency of expiration. By minimizing this difference in time, expiration with a minimal resistance is obtained. This is effectively provided by embodiments of the present invention.

In addition, a pre-defined safety margin may be provided in order to secure a sufficient gas volume available for reaching the set PEEP-level before the expiratory flow ends.

Accordingly, an expiratory target pressure reference curve is therefore used, which depends on how much of the inspired tidal volume of the same breath cycle has been currently expired during an expiratory phase of the same breathing cycle.

The shape of the target pressure curve 30 in section B is thus determined by how much of the inspired tidal volume VT$_i$ has been expired at a current point in time during the expiratory phase of the same breathing cycle.

A function determining the relationship of the target pressure curve 30 determined by how much of the inspired tidal volume VT; has been expired at a current point in time during the expiratory phase of the same breathing cycle has the following form.

During the expiratory phase, the target value for the expiratory pressure in the breathing apparatus to be adjusted by the expiratory pressure regulator 59 is adjusted according to the following function:

$$P_{target}(t) = f(V_{exp}(t), V_{insp}, V_{leakage}) \cdot PEEP_{set},$$

wherein $$f(V_{exp}(t), V_{insp}, V_{leakage}) \le 1;$$

$$V_{insp} = \int_0^{T_{insp}} \dot{V} \, dt$$

is the inspiratory tidal volume;

$$V_{exp}(t) = -\int_{T_{insp}}^t \dot{V} \, dt$$

is the accumulated, currently expired expiratory volume; and

V$_{leakage}$ is a leakage volume, e.g. due to leaking sealings, a leaking endotracheal tube, or other parts of the breathing circuit V$_{leakage}$ is for instance estimated by calculating the systemic leakage in the breathing apparatus and connected patient from an average leakage of a sequence of breath cycles prior to the current breath cycle. Optimally, V$_{leakage}$ is zero.

An embodiment is given as:

$$f(V_{exp}(t), V_{insp}, V_{leakage}) = \left(\frac{V_{exp}(t)}{(V_{insp} - V_{leakage}) \cdot k}\right)^n,$$

wherein
k is a positive numeral, and k≤1; and
n is a positive numeral, and n>1.

A higher value of n results in a quicker expiration.

A suitable value of n is determined by the performance capacity of the expiratory feedback control system.

The constant k indicates the desired safety margin and covers uncertainty of measurement as well as a reduced expiratory tidal volume due to the respiratory quotient (RQ).

The respiratory quotient (or RQ or respiratory coefficient), is a unitless number used in calculations of basal metabolic rate (BMR) when estimated from carbon dioxide production. The respiratory quotient (RQ) is calculated from the ratio RQ=CO$_{2\ produced}$/O$_{2\ consumed}$ The RQ can differ from 1, which results in a difference of inspired gas volume and expired gas volume without there being a leakage in the system.

In a further embodiment a function determining this relationship has the form of:

$$P_{target}(t) = \frac{V_{exp(t)} \times PEEP_{set} \times \text{margin}}{V_{insp}} + P_{accumulated}(t),$$

wherein
V$_{exp(t)}$ is the accumulated, currently expired expiratory volume;
V$_{insp}$ is the inspiratory tidal volume;
PEEP$_{set}$ is the desired PEEP level;
margin is a constant safety margin≥1; and
P$_{accumulated}$ is a term that continuously increases during the expiratory phase and is reset at the end of the expiratory phase; the algorithm only considers this term during curve section B, i.e. between time t$_A$ and time t$_B$, i.e. until the quasi stable PEEP$_{set}$ level is reached during regulation.

The term margin is a measure to define how much volume it is desired to have left in the lungs when PEEP$_{set}$ is reached, i.e. at the transition between curve section B and curve section C. However, regulation continues even during section C with a constant desired pressure value of PEEP$_{set}$.

A higher value for the term margin provides for a lower risk that available gas volume in the lungs is used up before PEEP is reached, leading to an abrupt pressure drop or bias flow trigg. However, this provides at the same time for a higher expiratory breathing resistance.

In the cases where the expired volume is lower than the inspired volume (x margin), the target pressure value will never reach PEEP level.

This may be compensated for by means of the P$_{accumulated}$(t) term that continuously increases during the expiratory phase and is reset at the end of the expiratory phase. This ensures that PEEP is reached under all conditions.

It will be appreciated that when the expiratory pressure regulator 59 is operated in dependence of this algorithm, the pressure in the expiration line 17 is allowed to initially fall below the level PEEP$_{set}$ at the beginning of the expiration phase, in the present embodiment calculated so that pressure within the lungs does not intentionally fall below $PEEP_{set}$.

The curve section B will thus always deviate from a straight line, but its shape is depending on the profile of the expiratory flow curve.

Curve section B will in particular cases increase more in the beginning of the expiratory phase than during later parts of the expiratory phase, i.e. it will flatten out towards $PEEP_{set}$. This is the case as the expiratory flow is normally higher in the beginning of the expiratory phase than at the end thereof, as for instance can be seen in FIG. 5.

As mentioned above, the present method and apparatus are not based on parameters or measurements between different breathing cycles, with the exception of the leakage estimation. The regulation is not iterative, but based on a breath by breath basis.

Regulation is performed in real time within a single breathing cycle.

Regulation may also be made in-vitro, i.e. without a connected patient, and entirely internally in the breathing apparatus. In this case the patient lung is replaced by a suitable device, e.g. a test lung, or similar mechanical arrangements having a compliance and resistance. Alternatively, the Y-piece may be plugged and flexible patient tubing having a compliance, serves as a resiliently fillable volume for gas supplied by the breathing apparatus during an inspiratory phase, which gas volume then is released during the expiratory phase until a desired PEEP is obtained.

Section C of Target Pressure Curve

The C portion of the target pressure value curve 30 is a portion of constant PEEP to a pre-defined value $PEEP_{set}$, e.g. selected by the user of the mechanical ventilator.

Section C extends from time $t_B$ to end of expiration.

The expiratory regulator is adjusted to allow a bias flow pass from the inspiratory branch 15 to the expiratory branch 17, wherein a gas flow out of patient 100 through conduit 57 is not allowed, keeping PEEP in the patient lungs at the desired level $PEEP_{set}$. The PEEP level is maintained until beginning of the next breathing cycle.

Still, there may be a certain gas volume left in the patient lungs, exceeding the functional residual gas volume that always is present in non-collapsed lungs. This gas volume may be present e.g. due to a safety margin that is chosen large, or if the patient has chosen a "short" inspiration that is explained further below. The control algorithm continues to regulate the expiratory pressure with a constant desired value, namely $PEEP_{set}$. A flow of gas out of the patient lungs may still occur during this phase.

Alternatively, the expiratory regulator is adjusted to stop any expiration of gas volume from the lungs of patient 100, e.g. an expiratory valve is completely closed.

Figure 6:
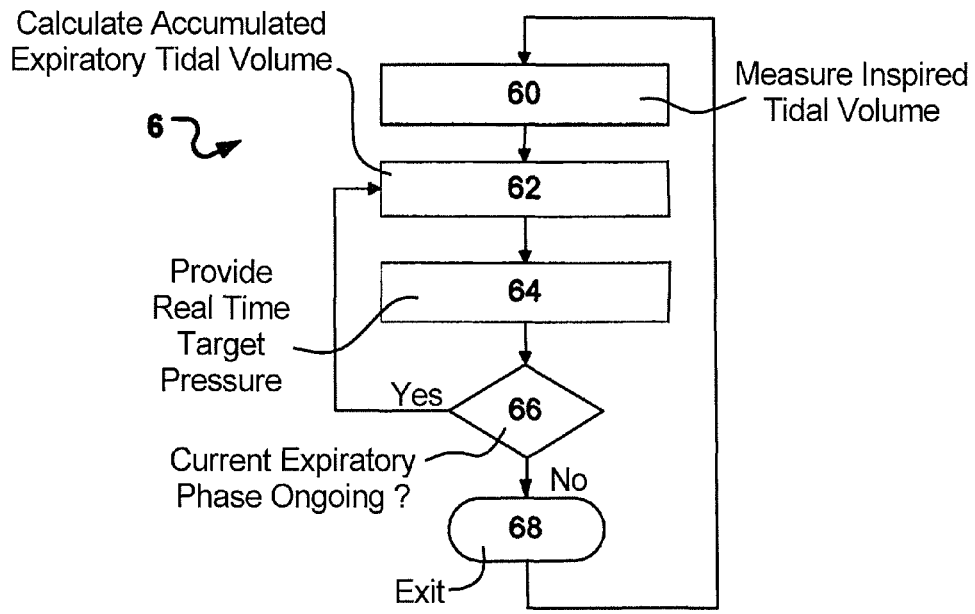
FIG. 6 is a flow chart illustrating a method of regulating expiratory pressure to a desired level of PEEP.

FIG. 6 is a flow chart illustrating a method in accordance with above for regulating an expiratory pressure to a desired PEEP level.

A method 6 is illustrated for internally controlling an expiratory pressure regulator 59 of a breathing apparatus 5 during an expiratory phase of a breathing cycle. The method 6 comprises measuring 60 an inspired tidal volume ($VT_i$) delivered from the breathing apparatus 5 during an inspiratory phase of the breathing cycle; and subsequently, during the expiratory phase, measuring a flow of expiratory gas by an expiratory flow sensor unit 152, calculating 62 an accumulated expiratory tidal volume ($VT_e$) of the expiratory phase, and providing 64 a real time target pressure to the expiratory pressure regulator 59 for regulating towards a desired positive end expiratory pressure (PEEP) level $PEEP_{set}$ based on the inspiratory tidal volume ($VT_i$) of the inspiratory phase of the same breathing cycle, and a currently accumulated expiratory tidal volume ($VT_e$). The control algorithm of the method 6 loops back at decision 66 to again calculating the current accumulated expiratory tidal volume ($VT_e$), as long as the current expiratory phase is ongoing. When the current expiratory phase is concluded, the method 6 exits at boundary 68, and may continue to a new inspiratory phase, as indicated by the dotted arrow in FIG. 6.

Figure 7:
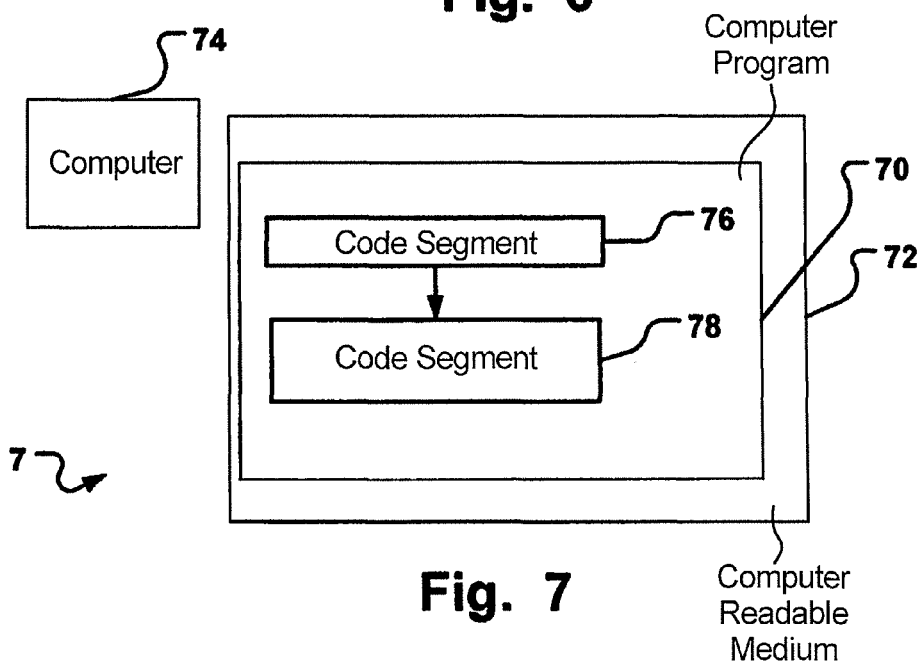
FIG. 7 is a schematic illustration of a computer program product for regulating expiratory pressure to a desired level of PEEP.

FIG. 7 is a schematic illustration of a computer program product for regulating expiratory pressure to a desired level of PEEP. A computer program 70 storable on a computer readable medium 72 for processing by a computer 74 is illustrated. The computer program 70 comprises code segments 76, 78 for of internally controlling the expiratory pressure regulator 59 of the breathing apparatus 5 during an expiratory phase of a breathing cycle. The code segments 76, 78 comprise a first code segment for measuring an inspired tidal volume ($VT_i$) delivered from the breathing apparatus 5 during an inspiratory phase of the breathing cycle; and a second code segment for subsequently, during the expiratory phase, measuring a flow of expiratory gas by an expiratory flow sensor unit 152, a third code segment for calculating an accumulated expiratory tidal volume ($VT_e$) of the expiratory phase, and a fourth code segment for providing a real time target pressure to the expiratory pressure regulator 59 for regulating towards a desired positive end expiratory pressure (PEEP) level ($PEEP_{set}$) based on the inspiratory tidal volume ($VT_i$) of the inspiratory phase of the same breathing cycle, and a currently accumulated expiratory tidal volume ($VT_e$).

As mentioned further above, the control algorithm of expiratory control unit 510 is based on a tidal volume control parameter. The control algorithm is adaptive to various conditions of this tidal volume control parameter.

The expiratory tidal volume $VT_e$ may under normal mechanical breathing conditions be substantially identical to the inspired tidal volume $VT_i$ of one and the same breathing cycle. $VT_e$ may also substantially deviate from $VT_i$, depending on various parameters, as will be explained below.

It may occur that a patient triggers an inspiration, early during an expiratory phase, a so-called "short" inspiration. The patient triggers thus a new inspiratory phase of the subsequent breathing cycle, without having expired the entire previously inspired tidal volume $VT_i$. This may in particular occur during assisted mechanical ventilation.

In case this occurs, that means expiratory tidal volume $VT_e$ differs from the inspired tidal volume $VT_i$ of one and the same breathing cycle, the present control algorithm as provided takes such difference into consideration.

In case of a "short" inspiration has been triggered by a patient, the patient has a surplus of gas volume left in its lungs from the earlier inspiratory phase. Thus, an expiratory tidal volume $VT_e$ of the breathing cycle starting with the "short" inspiration may be larger than the inspired tidal volume $VT_i$ of one and the same breathing cycle ($VT_e > VT_i$). This results in an earlier transition from curve B to curve C, shown in FIG. 4, which is not optimal. Thus, the positive effects related to reduced work of breathing by the control algorithm are reduced. However, work of breathing is still at least as low as for previously known control methods, as the control method during the entire expiration strives to keep the expiratory pressure constant at the level of $PEEP_{set}$.

It may occur that $VT_e < VT_i$. For instance, it may occur that a patient has inspired a tidal volume $VT_i$, and during the subsequent expiratory phase of the same breathing cycle, the patient does not expire this entire inspired volume. The patient may for instance hold its breath, such that the accumulated expiratory volume is substantially less than ($VT_i$–

$V_{leakage}$). The target pressure curve will here correspond to curve B. Consequently, the system will strive to adjust a pressure that is lower than $PEEP_{set}$. However, as the lung pressure is still higher than $PEEP_{set}$ due to the fact that the patient has entered the current breathing cycle from a level of $PEEP_{set}$ at the beginning of inspiration, then the patient has inspired a larger volume of gas increasing the lung pressure, and furthermore the inspired volume of gas is larger than the expired volume of gas that later on has been expired.

In case the expiratory pressure still should fall below $PEEP_{set}$, this may be due to the fact that the patient wants to breathe in, and the patient self decreases the pressure in the lungs during expiration. In this case, a new inspiration will be triggered. The current control algorithm also adapts to this situation and allows the patient to commence a new inspiratory phase.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The present invention may also be applied in a method of testing a PEEP regulation of a breathing apparatus when disconnected from a patient. Here, the method is applied as above, having the breathing apparatus e.g. connected to a test lung. The scope of the invention is only limited by the appended patent claims.

We claim as our invention:

1. A breathing apparatus comprising:
   a breathing circuit adapted to interact with a patient respiratory in successive breathing cycles each comprising an inspiratory phase and expiratory phase, to provide respiratory assistance to the patient, wherein the breathing circuit comprises an inspiratory gas flow section and an expiratory gas flow section, wherein the expiratory gas flow section includes an expiratory pressure regulator;
   an expiratory control unit configured to provide a real time variable target pressure ($P_{target}$) during an expiratory phase of a breathing cycle to said expiratory pressure regulator for regulating a desired positive end expiratory pressure (PEEP) level ($PEEP_{set}$) of said expiratory pressure regulator, said expiratory control unit being configured to provide said target pressure ($P_{target}$) based on an inspiratory tidal volume ($VT_i$) provided by said breathing circuit of an inspiratory phase in the same breathing cycle and a currently accumulated expiratory tidal volume; and
   said expiratory control unit being configured to provide said target pressure ($P_{target}$) below said desired PEEP level ($PEEP_{set}$) until an expiratory flow is zero or equal to a bias flow in said expiratory gas flow section of said breathing circuit.

2. The breathing apparatus of claim 1, wherein said expiratory control unit is configured to adapt to said patient and to changes in expiratory control conditions during or within said same breathing cycle in said respiratory assistance by said breathing circuit.

3. The breathing apparatus of claim 1, comprising an inspiratory flow sensor unit arranged to measure an inspiratory gas flow during an inspiratory phase of said same breathing cycle, and configured to provide said inspiratory tidal volume.

4. The breathing apparatus of claim 1, wherein said expiratory control unit is configured to control said expiratory pressure regulator so as to remain partly closed at a beginning of said expiratory phase in accordance with a condition that said expiratory pressure regulator is controlled to open not more than to provide said target pressure ($P_{target}$) with a maximum, pre-determined gradient.

5. The breathing apparatus of claim 1, wherein said expiratory control unit is configured to provide said target pressure ($P_{target}$) as $$P_{target}(t) = f(V_{exp}(t), V_{insp}, V_{leakage}) \cdot PEEP_{set}$$

wherein $$f(V_{exp}(t), V_{insp}, V_{leakage}) \leq 1;$$

$$V_{insp} = \int_0^{T_{insp}} \dot{V} \, dt$$

is the inspiratory tidal volume;

$$V_{exp}(t) = -\int_{T_{insp}}^{t} \dot{V} \, dt$$

is the accumulated, currently expired expiratory volume; and
   $V_{leakage}$ is a leakage volume.

6. The breathing apparatus of claim 5, wherein $$f(V_{exp}(t), V_{insp}, V_{leakage}) = \left( \frac{V_{exp}(t)}{(V_{insp} - V_{leakage}) \cdot k} \right)^n,$$

wherein
   k is a positive numeral, and $k \leq 1$; and
   n is a positive numeral, and $n > 1$.

7. The breathing apparatus of claim 1, wherein said expiratory control unit is configured to provide said target pressure ($P_{target}$) as $$P_{target}(t) = \frac{V_{exp(t)} \times PEEP_{set} \times \text{margin}}{V_{insp}} + P_{accumulated}(t)$$

wherein
   $V_{exp}(t)$ is the accumulated, currently expired expiratory volume;
   $V_{insp}$ is the inspiratory tidal volume;
   $PEEP_{set}$ is the desired PEEP level;
   margin is a constant safety margin $\geq 1$; and
   $P_{accumulated}$ is a term that continuously increases during the expiratory phase and is reset at the end of the expiratory phase.

8. A method of internally controlling an expiratory pressure regulator of a breathing apparatus during an expiratory phase of a breathing cycle, said method comprising:
   measuring an inspired tidal volume delivered from an inspiratory gas flow section of said breathing apparatus during an inspiratory phase of said breathing cycle; and
   subsequently, during said expiratory phase;
   measuring a flow of expiratory gas by an expiratory flow sensor unit of an expiratory gas flow section of said breathing apparatus;
   calculating an accumulated expiratory tidal volume of said expiratory phase;

providing a real time target pressure to said expiratory pressure regulator for regulating toward a desired positive end expiratory pressure (PEEP) level (PEEP$_{set}$) based on said inspiratory tidal volume of said inspiratory phase of said same breathing cycle, and a currently accumulated expiratory tidal volume; and providing said target pressure (P$_{target}$) below said desired PEEP level (PEEP$_{set}$) until an expiratory flow is zero or equal to a bias flow in said expiratory gas flow section of said breathing circuit.

9. The method of claim 8 comprising performing said method with a patient disconnected from said breathing apparatus.

10. The method of claim 8 comprising performing said regulation in-vitro with a mechanical arrangement having a compliance and resistance connected to said breathing apparatus at a patient connection thereof.

11. The method of claim 8, comprising plugging a patient connection of said breathing apparatus.

12. The method of claim 8, comprising adapting said regulation to a particular patient and to changes in expiratory control conditions during or within said breathing cycle in mechanical ventilatory assistance by said breathing apparatus.

13. The method of claim 8, comprising providing said inspiratory tidal volume from an inspiratory flow sensor unit measuring an inspiratory gas flow during an inspiratory phase of said breathing cycle.

14. The method of claim 8, wherein an expiratory control unit controls said expiratory pressure regulator to remain partly closed at a beginning of said expiratory phase in accordance with a condition that said expiratory pressure regulator is controlled to open not more than to provide said target pressure (P$_{target}$) with a maximum, pre-determined gradient.

15. The method of claim 8, comprising a providing of said target pressure (P$_{target}$) below said desired PEEP level (PEEP$_{set}$) until an expiratory flow is zero or equal to a bias flow in said expiratory gas flow section of said breathing apparatus.

16. The method of claim 8, comprising providing said target pressure (P$_{target}$) as $$P_{target}(t) = f(V_{exp}(t), V_{insp}, V_{leakage}) \cdot PEEP_{set}$$

wherein $$f(V_{exp}(t), V_{insp}, V_{leakage}) \leq 1;$$

$$V_{insp} = \int_0^{T_{insp}} \dot{V} \, dt$$

is the inspiratory tidal volume;

$$V_{exp}(t) = -\int_{T_{insp}}^{t} \dot{V} \, dt$$

is the accumulated, currently expired expiratory volume; and

V$_{leakage}$ is a leakage volume.

17. The method of claim 16, wherein $$f(V_{exp}(t), V_{insp}, V_{leakage}) = \left( \frac{V_{exp}(t)}{(V_{insp} - V_{leakage}) \cdot k} \right)^n,$$

wherein k is a positive numeral, and k≤1; and n is a positive numeral, and n>1.

18. The method of claim 8 comprising providing said target pressure (P$_{target}$) as $$P_{target}(t) = \frac{V_{exp(t)} \times PEEP_{set} \times \text{margin}}{V_{insp}} + P_{accumulated}(t)$$

wherein

V$_{exp(t)}$ is the accumulated, currently expired expiratory volume;

V$_{insp}$ is the inspiratory tidal volume;

PEEP$_{set}$ is the desired PEEP level;

margin is a constant safety margin ≥1; and

P$_{accumulated}$ is a term that continuously increases during the expiratory phase and is reset at the end of the expiratory phase.

19. A non-transitory computer-readable storage medium encoded with programming instructions, said storage medium being loaded into a computerized control system of a breathing apparatus, and said programming instructions causing said computerized control unit to control an expiratory pressure regulator of the breathing apparatus during an expiratory phase of a breathing cycle by:

initiating measurement of an inspired tidal volume delivered from said breathing apparatus during an inspiratory phase of said breathing cycle; and subsequently, during said expiratory phase;

initiating measurement of a flow of expiratory gas by an expiratory flow sensor unit;

calculating an accumulated expiratory tidal volume of said expiratory phase;

providing a real time target pressure to said expiratory pressure regulator for regulating toward a desired positive end expiratory pressure (PEEP) level (PEEP$_{set}$) based on said inspiratory tidal volume of said inspiratory phase of said same breathing cycle, and a currently accumulated expiratory tidal volume; and providing said target pressure (P$_{target}$) below said desired PEEP level (PEEP$_{set}$) until an expiratory flow is zero or equal to a bias flow in said expiratory gas flow section of said breathing circuit.

\* \* \* \* \*